United States Patent [19]
Ashmead et al.

[11] Patent Number: 5,162,369
[45] Date of Patent: Nov. 10, 1992

[54] COMPOSITION AND METHOD FOR ENHANCING THE IMMUNE SYSTEM IN WARM-BLOODED ANIMALS EXHIBITING SYMPTOMS OF ANTIGENIC MORBIDITY

[75] Inventors: H. Dewayne Ashmead, Fruit Heights; Harvey H. Ashmead, Kaysville; Robert B. Jeppsen, Layton, all of Utah

[73] Assignee: Brigham Young University, Provo, Utah

[21] Appl. No.: 549,112

[22] Filed: Jul. 6, 1990

[51] Int. Cl.$^5$ .................. A61K 31/28; A61K 31/315; A61K 31/30; A61K 31/295
[52] U.S. Cl. .................................. 514/492; 514/494; 514/499; 514/502; 514/561
[58] Field of Search ............... 424/630, 639, 641, 646; 514/492, 494, 499, 502, 561

[56] References Cited
PUBLICATIONS
Chem Abst, 46544y (1972). Abuzarov et al.
J. Am. Chem. Soc 1981, 103 7026–7028. Hemmi et al.

*Primary Examiner*—Frederick E. Waddell
*Assistant Examiner*—Zohreh A. Fay
*Attorney, Agent, or Firm*—Thorpe, North & Western

[57] ABSTRACT

A method for maintaining the immune system of a warm-blooded animal afflicted with a form of antigenic morbidity exacerbated by intestinal malabsorption of minerals is disclosed. Minerals selected from the group consisting of copper, zinc, manganese, iron and selenium are provided in the form of amino acid chelates having a ligand to mineral ratio of at least 1:1, a molecular weight of no more than 1500 and a stability constant of between about $10^6$ and $10^{16}$ and administered orally. They are absorbed from a portion of the intestinal tract other than that utilized for the absorption of cations. The method is particularly adapted to the maintaining of the immune system of a warm-blooded animal infected by a virus which compromises the absorption of trace minerals via the normal cationic absorption route. The presence of intestinal malabsorption in the host showing symptoms of antigenic morbidity is first confirmed. Based on previous data of mineral levels and ratios in assayed tissues and/or body fluids of similarly infected hosts compared with mineral levels and ratios in healthy hosts, an amino acid chelate composition is formulated and administered to the afflicted animal(s) for such time as is necessary for the immune system to be properly maintained.

19 Claims, No Drawings

COMPOSITION AND METHOD FOR ENHANCING THE IMMUNE SYSTEM IN WARM-BLOODED ANIMALS EXHIBITING SYMPTOMS OF ANTIGENIC MORBIDITY

BACKGROUND AND FIELD OF THE INVENTION

This invention relates to compositions and methods of enhancing the immune system in warm-blooded animals showing symptoms of antigenic morbidity. More particularly, this invention relates to amino acid chelated mineral compositions containing one or more minerals selected from the group consisting of copper, zinc, manganese, iron and selenium and to methods of administering these compositions to influence mineral uptake and absorption in warm-blooded animals exhibiting symptoms of antigenic morbidity with the resultant strengthening of the immune system of the animal.

Metabolic dysfunctioning in warm-blooded animals may h=indicated by a variety of overt symptoms or signs. General malaise, increased morbidity and/or mortality, poor food conversion and/or loss of weight and sterility, among others, are indications of compromised metabolic functioning. One of the causes of metabolic dysfunctioning is an inadequate immune system brought on or hampered by antigenic morbidity. By "antigenic morbidity" is meant that the health and well-being of the warm-blooded animal is compromised by a disease initiated or worsened due to the presence of an entity displaying an antigen. With the exception of antigens of autoimmune origin, an antigen is a foreign substance, usually a protein or carbohydrate, which, when introduced into the body, provokes an immune system response which stimulates the production of antibodies or immunoglobulins. An inadequate immune system may be the result of insufficient development of the system or the breakdown of the system resulting from viral, bacterial or other antigenic infections. Most antigens of immediate concern are foreign protein or carbohydrate substances such as viruses, bacteria, protozoa and molds. In simple terms, when an entity displaying an antigen enters the body, there is recognition of the antigen by the immune system which stimulates synthesis of circulating antibodies (immunoglobulins) specific to the antigen. Many of these cellular responses are controlled by enzyme systems which have a trace element at their core. Manganese, copper and zinc are examples of co-factors in the enzymes controlling proper immune functioning. Iron and selenium may also play important roles. Iron deficiency is associated with impaired cell-mediated immunity. Investigations with selenium have shown that it can produce stimulatory effects on the immune response.

Viral and other infections sometimes overwhelm the immune system leading to secondary complications which tend to exacerbate the primary infection. For example, some infections cause morphological changes in the intestine which result in malabsorption which may hinder the uptake of the metallic cofactors which are beneficial for immune system functioning. A common site of intestinal abnormality is the duodenum, the portion of the small intestine where metal ions are primarily absorbed under normal conditions. Since the pH in the duodenum is acidic, metal ions are present in soluble ionic form. As these ions pass along the intestinal tract, the pH in the jejunum becomes more basic and absorption of metals in ionic form becomes more difficult. Diarrhea is also a common problem associated with many infections due to the profuse fluid secretion in the duodenum and proximal jejunum resulting in malabsorption of minerals.

An extreme viral infection currently of major concern is popularly referred to as AIDS (acquired immune deficiency syndrome). More appropriately it is an HIV (human immunodeficiency virus) infection leading to AIDS. This disease proceeds through various stages from HIV exposure to HIV infection and on to development of AIDS. These stages are classified by Redfield, et al. in an article entitled "The Walter Reed Staging Classification for HTLV-III/LAV Infection" published in the New England Journal of Medicine, Volume 314, Page 131, January, 1986 and are referred to as the Walter Reed (WR) classification. They are thus referred to as WR0 through WR6. The WR0 classification means there has been exposure to the HIV virus although there are no symptomatic indications. WR1 means there is a positive HIV antibody and/or virus determination but no other symptoms. A WR2 classification is characterized by chronic lymphadenopathy or swollen lymph nodes in addition to positive HIV antibody and/or virus determination. A WR3 classification is reached when the T4-cell count drops below 400 cells per cubic millimeter of blood and stays down. The normal T4-cell count is about 800. There may or may not be chronic lymphadenopathy in WR3 through WR6 classifications but the T4-cell count stays below 400. A patient moves to the WR4 stage after partial sub-clinical (asymptomatic) defects are found in delayed hypersensitivity, i.e. the ability to react to skin tests that are a barometer of immune functioning. The line into WR5 is crossed when the patient completely fails to respond to the skin test or when thrush (a fungal disease of the mouth) develops. Lymphadenopathy and abnormalities of the T4-cell and skin tests must persist for at least three months to serve as valid criteria. Patients enter into the WR6 stage and are said to have AIDS when opportunistic infections, which occur because the immune system has broken down, such as cryptococcal meningitis, develop elsewhere in the body.

The HIV virus is a retrovirus which does not per se cause death of its host. However, the presence of the HIV virus contributes to the decline of T4-cells in the body. The T4 lymphocytes, or T4-cells, recognize foreign antigens or infected cells. Upon recognition, the T4-cells help activate another set of white blood cells called B-lymphocytes. These B-cells then multiply and produce specific antibodies that bind to the infected cells and other organisms containing the antigen. The binding of the antibodies to the antigen displaying cells or organisms inactivates and/or destroys those cells or organisms.

The T4-cells have other functions as well. They orchestrate cell-mediated immunity by killing infected cells with cytotoxic cells such as T8 lymphocytes and white cells known as natural killer cells. The T4-cells also influence mobile scavenger cells known as monocytes and macrocytes. These scavengers engulf infected cells and foreign particles and secrete a variety of cytokines. The cytokines are small but highly potent proteins that modulate the activity of many cell types, including T and B cells. The T4-cells also secrete cytokines on their own which stimulate the proliferation of T and B cells in the body.

T4-cells require the presence of trace minerals for their production. However, in cases of HIV infection, there is malabsorption of cationic minerals which leads to a decrease in the T4-cell production. From the above, it is apparent that the loss of T4-cells can seriously impair the body's ability to fight antigen caused infections and viral infections, in particular. The eradication of these invading organisms requires a highly-orchestrated cell-mediated response. Without T4-cells this immune response does not function satisfactorily.

According to Redfield et al., "HIV Infection: The Clinical Picture," Scientific American, 259:90, October, 1988, there is a balance of power between the HIV virus and the immune system arranged by the T4-cells. From the WR0 (exposure stage) to the WR1 stage the HIV virus increases rapidly at which point the immune system begins to respond. By the time the WR2 stage is reached the viable virus in the body has dropped dramatically with the concomitant rise in scavengers, macrophages, T-cells, B-cells, antibodies and other immune system members. The immune system remains somewhat in control throughout the WR2 and into the WR3 stages although there is a gradual rise in HIV. However, by the time the WR4 stage is reached, the HIV has begun to overwhelm the immune system and the T4-cells become so depleted that the balance of power switches and from that point on, the HIV replicates wildly, overwhelming the remaining T4-cells and any vestiges of immune defense.

The retrovirus pattern shown by the HIV virus in going from stage to stage until the T4-cells are no longer able to function raises unanswered questions. Why is the retrovirus initially dominant at first only to be controlled during the first few stages of the infection? In other words, if the retrovirus is destroying T4-cells in excess of what the immune system has, why does the immune system suddenly become more dominant as the individual moves into the WR2 and even into the WR3 stages? It could be argued that the HIV virus destroyed so many T4-cells that the immune system was no longer able to dominate. However, that argument is flawed in that the retrovirus was dominant in the WR1 stage only to yield to the immune system during the WR2 and WR3 stages and into the WR4 stage. This suggests that the immune system was able to control the retrovirus until such time that some event occurred to the host or the immune system of the host to inhibit the continued control of the retrovirus.

It is known that as the HIV infection progresses from stage to stage, the retrovirus is responsible for morphological changes in the intestine resulting in malabsorption of essential nutrients. While not known for a certainty, it is believed that trace minerals, in particular, are inadequately absorbed. This, in turn, prevents the immune system from regeneration to the degree necessary to continue to fight the onslaught of the retrovirus as the disease goes from stage to stage. As previously stated, manganese, copper and zinc are the primary co-factors in the enzymes controlling proper immune functioning and iron and selenium are also factors which may be necessary. The production of any new cell, including the all important T4-cells, requires DNA and RNA. Zinc is essential for the production of these nucleic acids through activating the enzymes DNA polymerase and RNA polymerase. In the absence of zinc, cell mitosis is blocked.

Heise, et al, "Jejunal Dysfunction Associated with Human Immunodeficiency Virus (HIV) Infections", J. Am. College Nutr., 7:406, 1988, report that the HIV virus causes malabsorption. This is caused in part by abnormal interocyte function as reflected by immaturity, decreased cell density and low enzyme activity. These abnormalities in the intestinal tract are independent of the stage of the HIV infection. Endoscopy of 200 patients treated for HIV infections as reported by Heise, et al., "Gastrointestinal Befunde bei der HIV-Infektion. Klinik, Mikrobialogische Befunde und Endoskopisches Erscheinungsbild", Ptsch. Med. Worchenschr, 113:1588, 1988, revealed that in 60%, there were mucosal changes. Wall, et al., "Multifocal Abnormalities of the Gastrointestinal Tract in AIDS", A.J.R. 146:1, 1986, reported that the most common site of intestinal abnormality was the duodenum which is the portion of the intestinal tract where metal ions are generally absorbed. The mucosal changes noted by Wall, et al, supra, include thickened folds, modularity, increased secretions, superficial erosions, ulcerations, plaque formation and tumor mass. It was further noted that, upon closer examination of the duodenums of patients infected with HIV virus, the infected cells were located in both the crypts and the lamina propria, suggesting that the HIV virus may contribute to some of the gastrointestinal disorders noted above.

One factor which may contribute to the malabsorption syndrome in HIV related illness is that ionic mineral absorption requires an integral protein carrier molecule embedded in and transversing the mucosal membrane. Once absorbed into the mucosal cell the transfer of the cation from the terminal web below the microvilli to the basement membrane requires the presence of carrier proteins. For iron and most minerals apoferritin is a suitable carrier. In the case of zinc, albumin is the carrier protein. For copper the carrier is ceruloplasmin and for manganese it is transmanganin. In some HIV infected patients there is the development of Kaposi's sarcoma, a type of tumor that erupts on the mucosal wall. These tumor cells are derived from membrane cells in the mucosa rather than from the lymph cell. Laine, et al., "Protein-losing Enteropathy in Acquired Immunodeficiency Syndrome due to Intestinal Kaposi's Sarcoma,", Arch. Intern. Med., 147:1174, 1987 report that Kaposi's sarcoma caused a loss of protein and albumin that could have potentially been used to transport metal ions from the small intestine wherever the sarcoma existed, providing further evidence of duodenal malabsorption of minerals in HIV infected patients who have developed this sarcoma. Both protein and albumin are necessary to transport mineral ions from the gut to the plasma.

Similar malabsorption problems are manifest in other species of warm-blooded animals, such as chickens, infected with reovirus as opposed to a retrovirus.

If the immune system is suppressed or does not function properly the chemistry of the cells is altered and the cells do not perform their tasks due to mineral deficiencies.

From the above it is evident proper metabolic functioning of minerals such as copper, zinc, manganese, iron and selenium play an important role in maintaining the immune system. Moreover, it is also evident that there may be metabolic dysfunctioning of cells on the surface of the intestinal lumen to the point that these minerals may not be adequately absorbed in warm-blooded animals, including humans. This could occur if the animal were suffering from antigenic morbidity which affected the portion of the intestine where mineral ions were most likely to be absorbed, i.e. the duodenum. Over a period of time, the inability of the body to absorb these minerals would result in compromising the immune system and allowing secondary diseases to be introduced into the body. It would therefore be beneficial to provide essential minerals to warm-blooded animals exhibiting symptoms of metabolic dysfunctioning due to antigenic morbidity in a bioavailable form in which such minerals would be absorbed via a pathway which did not require duodenal absorption in ionic form.

Ashmead et al., U.S. Pat. No. 4,020,158; Ashmead, U.S. Pat. No. 4,076,803; Jensen U.S. Pat. No. 4,167,564; Ashmead, U.S. Pat. No. 4,774,089 and Ashmead, U.S. Pat. No. 4,863,898 all teach various uses for amino acid chelates in reference to increasing absorption of essential minerals into biological tissues. Some of these patents suggest that certain mineral and ligand combinations can enhance metal uptake in specific organs or tissues where specific biological functions are enhanced, i.e. minerals crossing the placental membranes into foeti, estrus or spermatogenesis, etc. However, it has not heretofore been known that a biological system, as distinguished from tissues, can be affected directly through the proper administration of amino acid chelates. By definition, a system is a set or series of interconnected or interdependent parts or entities (objects, organs, fluids, organisms, etc.) that function together in a common purpose or produce results impossible of achievement by one of them acting or operating alone. Hence, there is greater complexity involved in affecting a system in order to influence or assist in the enhancement, maintaining or strengthening of such a system as compared to influencing mineral uptake or to the direction of minerals to certain tissue sites.

OBJECTS AND BRIEF SUMMARY OF THE INVENTION

It is an object of the present invention to provide to a warm-blooded animal, negatively affected by a form of antigenic morbidity, with one or more bioavailable trace minerals selected from the group consisting of copper, zinc, manganese, iron and selenium in such quantities and ratios as are required to repair and maintain the proper functioning of the immune system of the animal.

It is also an object of the present invention to provide a method of minimizing antigenic morbidity in warm-blooded animals exacerbated by intestinal malabsorption of minerals and bolstering the immune system by means of administering to said animals, sufficient minerals in a bioavailable form which can be absorbed from a portion of the intestinal tract other than the duodenum through the utilization of a different pathway for their uptake, rather than the pathway employed by cations.

These and other objects may be accomplished by the proper formulation of one or more minerals selected from the group consisting of copper, zinc, manganese, iron and selenium and the administration of one or more of these minerals to a warm-blooded animal afflicted by a form antigenic morbidity, particularly when exacerbated by intestinal mineral malabsorption. By proper formulation is meant the providing of such minerals in a form which is bioavailable to the animal at intestinal absorption sites other than those utilized strictly for cationic absorption. Also, the ratio of one mineral to another may be significant and can vary depending upon the species of animal and the form and/or stage of antigenic morbidity.

Bioavailable forms of copper, zinc, manganese, iron and selenium which are absorbed via the intestinal tract of a warm blooded animal at a site other than the cation absorption sites in the duodenum are those made by chelating the mineral with an amino acid or peptide ligand wherein the ligand to mineral ratio is at least 1:1 and preferably 2:1 or higher and wherein the molecular weight of the amino acid chelate formed is not greater than 1500 and preferably does not exceed 1000. Such amino acid chelates are stable and are generally absorbed intact through the intestinal tract via active dipeptide transport. Such amino acid chelates have a stability constant of between about $10^6$ and $10^{16}$. A more detailed description of such chelates and the method by which they are absorbed is found below and is also documented in Ashmead et al., U.S. Pat. No. 4,863,898 which issued Sep. 5, 1989 and also in Ashmead et al., Intestinal Absorption of Metal Ions and Chelates, Published by Charles C. Thomas, Springfield, Ill., 1985.

DETAILED DESCRIPTION OF THE INVENTION

As documented by the Ashmead et al. publication, referenced above, mineral absorption from the intestinal tract occurs via at least two pathways. A mineral salt, after ingestion is solubilized and ionized in the acid pH of the stomach. The metal cations passing from the stomach into the intestinal tract are absorbed, if at all, in the duodenum or upper portion of the small intestine. This requires a relatively low acid pH. It is believed that the metal cation is presented to the integral proteins in the brush border of mucosal cells of the duodenum. The transport of the metal ion across the mucosal cell membrane is accomplished by chelating or complexing the cation to complex carrier proteins. This binding commences the activation of an enzymatic system called a "pump". Several enzyme reactions occur in which the cation is moved from molecule to molecule within the system. This movement is very rapid and stops when the cation is delivered to the interior side of the mucosal membrane where the metal cation is released and rechelated by cytoplasmic proteins, such as apoferritin, in the case or iron; ceruloplasmin in the case of copper; transmanganin in the case of manganese and albumin in the case of zinc. The cation chelated with cytoplasmic protein is then carried to the basement membrane of the mucosal cell. Metal ions absorbed in this manner are reacted, released, re-reacted and re-released repeatedly during this transport from the intestinal tract to the portal blood.

Metal cations which are not absorbed via the duodenum descend on through the intestine to where the pH is increased. As the pH increases, the metal ions lose their soluble characteristics and react with phytates, phosphates, hydrophides and other anions to form insoluble precipitates which pass through the gut and are excreted in the feces.

The Ashmead et al. publication documents that when an impermeant substance, such as a metal cation is chemically linked to an amino acid or low molecular weight peptide, the resulting complex can be transported via a peptide transport system across the cell membrane. This has been referred to as having the impermeant substance "smuggled" across the membrane and the complex has accordingly been referred to in the literature as a "smugglin". These are the amino acid chelates above referred to having a ligand to mineral ratio of at least 1:1 and preferably 2:1 or greater, a molecular weight of no more than 1500 and preferably not more than 1000 and a stability constant of between about $10^6$ and $10^{16}$ In the field of animal nutrition, the American Association of Feed Control Officials has issued the following official definition: "amino acid chelate—a metal ion from a soluble salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800." It is also documented that amino acid chelates can be prepared from metal ions which do not come from soluble salts. Ashmead, U.S. Pat. No. 4,599,152 and Ashmead, U.S. Pat. No. 4,830,716 both disclose methods of preparing pure amino acid chelates using metal sources other than soluble metal salts. However, it is not critical to the present invention which manner the amino chelates are made provided they meet the criteria stated above.

While it is known that nutrition plays an important role in proper cellular physiology and maintenance of the immune system, it is probably the least understood factor in cellular biology. Researchers are just beginning to understand that trace element nutrition, or malnutrition as the case may be, is often the core of immune system problems. If manganese, zinc, iron, selenium and copper are deficient, the immune system will be deficient. Even if these trace minerals are present in sufficient amounts in the diet, an overabundance of certain other trace minerals can interfere with their absorption. See, for example, Miller, "Trace Minerals-Role of Zinc, Iron and Selenium in Swine Immunity", Feed Management Vol 40, pp 20 (1989). Also, as referenced above, the form of the nutrient is often more important than the quantity. Elemental salts are not as bioavailable as the amino acid chelates referred to, particularly when there is interference from heavy metals. If the immune system is not functioning properly, many of the drugs and/or methods relied on to treat and prevent disease are ineffectual and mortality may result.

Copper, zinc, manganese, iron and selenium are minerals of greatest concern and have a direct impact on maintaining the immune system. Besides being present in adequate quantities, the interrelationship of one mineral to another is important. Specific minerals may be present in adequate amounts according to assays. However, due to interference or competition, such minerals may not be biologically available or in proper balance. For example, it is known that excess molybdenum directly ties up copper. Manganese and iron compete for active ionic absorption sites in the small intestine. Manganese is readily excreted from the body, but there is no similar excretion mechanism for excess iron accumulation which also has an inhibitory affect on copper utilization.

The amino acid compositions will preferably be administered to the warm blooded animal orally. In many cases mixture of the chelates in the food, drinking water or other ration form given to the animal may be used. For example, the chelates may be mixed with salt (sodium chloride) when being administered to the bovine species. They may similarly be mixed with feed or rations destined for general animal or livestock usage. In the case of humans, the chelates may be administered in the form of tables, capsules, powders, syrups, elixir or any other suitable form. They may be mixed with fillers, excipients, vitamins and other foodstuffs.

The exact amount of mineral to be administered, and the ratio of one mineral to another, will depend upon animal species and the particular form of antigenic morbidity and the symptoms displayed. Often, assay results of samples of tissue, serum or other body fluid may have to be taken before a proper formulation can be made. To make a determination, the correct interpretation of data may be more important than the actual numbers generated in an assay and values must be correlated to bioavailability and antagonistic parameters of one trace element to another or from one trace element to other minerals such as copper and iron. An assay of the diet may also be important to determine mineral amounts in the diet and identify deficiencies and/or antagonistic factors which may affect trace minerals when administered.

Therefore, the exact amount of amino acid chelate, which minerals to use and in what ratios, are preferably determined on an empirical basis according to need. Hence, the term, "effective amount" of one or more minerals is based on both the amount of mineral and the ratio of one mineral to another which has been determined to be required to meet the needs of a particular warm-blooded animal or group of animals, including humans, exhibiting certain symptoms of metabolic dysfunctioning brought on or affected by antigenic morbidity. In some instances, based on collected data over periods of time, it will be possible to preformulate compositions based on known needs of the animal species afflicted with certain forms or being at certain stages of antigenic morbidity. However, one skilled in the art, based on the information provided herein, can determine without undue experimentation what an "effective amount" of a composition is and how to administer it accordingly. It is not possible to categorically state that "x" mg of trace mineral per kg of animal body weight is what is needed to maintain immunity. Nor is it possible to state, for example, that the ratio of Cu to Zn will be "a:b" in all instances. Each animal species and form of antigenic morbidity may require different amounts of minerals and/or ratios of minerals. The stage of the affliction may also affect the "effective amount". For these reasons, a data bank of various trace mineral levels and ratios which are found in various forms of antigenic morbidity according to animal species and a comparison these data against mineral levels and ratios found in healthy animals of the same species is being compiled. From these data the "effective amounts" of minerals to administer will be available. For animal species in which an RDA [recommended daily allowance], or similar nutritional guideline, has been established, that amount may be used as a minimum or threshold "effective" amount to be administered to that species. However, in some instances, it may be possible to administer even lesser amounts which are also "effective" provided the correct mineral ratios are used. Furthermore, an RDA supposes to examine all sources of a mineral ingested by the host. In the present invention, supplementation will be in addition to that contained in food sources. Therefore, an "effective amount" of a mineral may be administered consisting less than an established RDA. If the mineral ingested is considered in all forms, i.e. foods, supplements, etc., the total amount of mineral administered, in amino acid chelated form, and as other organic or chelated forms and inorganic forms, may actually exceed an RDA.

The following examples are illustrative of the invention showing treatment of warm-blooded animals suffering from symptoms of antigenic morbidity wherein the immune responses in these animal species are improved through the utilization of copper, manganese, zinc, iron and selenium amino acid chelates administered alone or in combination.

EXAMPLE 1

A two year study of calf morbidity and mortality was conducted involving calves from a Limousin cow herd. The annual calf losses were ranging between 12 and 20% prior to the study. More calves born in the spring were dying than calves born in the fall and most mortality occurred between three and ten weeks of age.

During the fall of the first year of the study, the cows were subjected to a preventative vaccination program in hopes of reducing spring calving mortality. When the calves were born in the spring, they were also vaccinated. The first spring was cold and rainy and the cows and the 66 calves born were housed in barns during inclement weather. When weather permitted the cows and calves were allowed to graze in a rye grass pasture. By mid spring, many of the older calves had developed pneumonia. Response to conventional treatment was fair, initially, but pneumonia recurred and new cases of pneumonia and scours developed. The calves started dying. Post mortem findings included enteritis, FA positive for coronavirus and pneumonia. Despite treatment with injectable antibiotics on three occasions, at the end of May only 58 calves survived. It was suspected that an immunologic disorder could be the cause of the problems.

Based on several studies, Table 1 gives the desired bovine immunoglobulin levels based on age:

TABLE 1

| Age: | mg/ml | | |
|---|---|---|---|
| | IgG1 | IgG2 | IgM |
| Newborn | 24–50 | 0.2–0.8 | 1.0–5.0 |
| 1–2 Weeks | 15–35 | 0.2–0.6 | 0.6–1.0 |
| 1 Month | 15–29 | 0.1–1.5 | 0.4–0.8 |
| 2 Months | 8–14 | 0.1–2.0 | 0.7–1.7 |
| 3 Months | 10–16 | 0.1–2.1 | 1.8–3.2 |
| 6 Months to Adult | 6–14 | 0.4–2.1 | 1.7–2.9 |

All 58 calves living at the end of May were bled and tested for specific levels of IgM and the (IgG1+IgG2)/IgM ratio utilizing immunodiffusion kits. Of the calves tested 67% were found to be IgM deficient. Thirty six days later, the test was repeated in hopes that greater maturity of the calves would result in a normal IgM level. This was not found, the IgM of one calf, previously normal, had dropped to abnormal levels and seven other calves dropped from abnormally low to critically low levels. One calf, initially normal, remained so and three others rose, over time, to normal levels. It was noted that those calves which showed a decrease in IgM over the 36 day testing period were generally in poorer health than the rest of the herd. The total mortality of the spring calves born was 22% and the morbidity was 67%.

It was noted, in measuring IgG immunoglobulin and comparing their levels to the normal levels given above, that, as an aggregate, their levels were abnormally high. IgG and IgM antibodies account for about 80% of all the immunoglobulins produced by the body. In the usual situation, upon initial antigen stimulation, IgM is normally produced. As a membrane-bound molecule on the lymphocytes, it serves as the first line of defense against the antigens by mediating the response of the B lymphocytes to the antigen stimulation. Because of the large molecular size of IgM (mole wt. about 900,000 daltons) these antibodies are confined primarily to the blood. The presence of IgM in the blood contributes to its service in the first line of immunological defense. The secondary immune response comes from the IgG class of antibodies which constitute about 70% of the total immunoglobulins produced. The IgG class resides in high quantities in the blood but, because of smaller molecular size (mole wt. about 180,000 daltons), it can more easily depart the blood stream to enter spaces between the tissues as well as through body surfaces. As IgM levels decline, the IgG increases upon secondary stimulation. A second exposure to the same antigen results in a secondary, or anamnestic response in which IgM levels, which were once declining, increase, as does the IgG immunoglobulin. In the tests conducted, the IgM levels did not increase although the IgG levels did, thereby producing an imbalance in the IgG/IgM ratios with a consequent lowering of immune system effectiveness.

By the time the spring calving analysis was completed, fall calving had begun in this herd. It was decided to test the fall calves and compare them with the spring calves. There were 28 calves born in the fall season of which 5 eventually died. When the calves attained an average of 107 days they were bled and their IgM and IgG levels were measured. Of these calves, 83% were IgM deficient. An analysis of the calves' IgG2 revealed that it had surged, as in the case of spring calves, when the IgM levels were below normal. These data suggest that the fall calves also had a deficient immune system.

Since treatment with vaccination, antibiotics and other drugs had not improved the herd health, which in fact, had worsened, it was decided to initiate a test nutritional program utilizing a supplementation of copper, zinc and manganese administered as amino acid chelates in an attempt to strengthen the immune systems of calves born in this herd to within normal limits. The amino acid chelates had a ligand to metal ratio of about 2:1 and an average molecular weight which did not exceed 1000. The chelates were formulated to be administered in the feed of the entire cow/calf herd, such that the average daily mineral consumption (in grams) would be as shown in Table 2:

TABLE 2

| Animal Type | Copper | Manganese | Zinc |
|---|---|---|---|
| Lactating Cows | | | |
| First 90 days | .18 | .36 | .72 |
| Second 90 days | .13 | .26 | .52 |
| Last 125 days | .10 | .19 | .32 |
| Dry Cows | .09 | .17 | .34 |
| Dairy Calf Starter | .04 | .08 | .16 |
| Growing Heifers | .07 | .14 | .28 |
| Bulls | | | |
| Continuous | .07 | .14 | .28 |
| 50 days prior to and through breeding | .13 | .26 | .26 |

The following year when the calves that were born in the spring had reached an average age of 165 days, they were bled and their IgM and IgG levels measured. They had a mean IgM of 1.10 mg/ml with a standard deviation of 0.4 mg/ml. This was a considerable improvement over the previous spring calf herd which had mean IgM levels of 0.62 mg/ml with a standard deviation of 0.53 mg/ml. When IgG2 was measured after the amino acid chelate supplementation, it averaged 2.43 with a 0.62 deviation as compared to a 1.65 with a 2.13 deviation prior to supplementation. The mean amount of IgG1 after supplementation was 10.43 mg/ml with a 2.13 deviation compared to a 10.98 mg/ml with a 6.05 deviation before supplementation.

The calves born in the fall were also assayed. Their mean IgM and IgG levels continued to improve. The mean IgM level was 1.76 as compared to 0.91 a year earlier. The results of the entire study are summarized in Table 3 as follows:

TABLE 3

| Mean | Year 1 Before Supplementation | | Year 2 After Supplementation | |
|---|---|---|---|---|
| | Spring | Fall | Spring | Fall |
| Morbidity (%) | 67 | 54 | 11 | 0 |
| Mortality (%) | 22 | 17 | 2 | 0 |
| IgM (mg/ml serum) | .66 | .91 | 1.09 | 1.76 |
| IgG:IgM | 50.5 | 16.1 | 13.9 | 9.4 |

The dramatic changes seen in the above table did not occur until the mineral nutritional changes were made which were the only changes made in the program. General improvement in the condition of the entire herd, including the cows and bulls was also seen, but no data were maintained to quantify these improvements. While the precise biochemical function of copper, zinc and manganese were not determined from this study, it is apparent that, as the IgM titers were elevated and the IgG/IgM ratios decreased, there was a corresponding drop in morbidity and mortality. It has been observed that, in almost every case of clinical disease, the IgM level is below normal, and the IgG levels (IgG1 +IgG2) are very high. Under most circumstances the IgG:IgM ratios in bovine species should vary from about 1:1 to 15:1. In problem herds the ratios can go as high as 100:1. It will be noted that when the ratios dropped into the normal range, the morbidity and mortality were significantly lower than when ratios were outside that range.

EXAMPLE 2

This example reports a field trial test relating trace mineral levels and sources to the immune response and involves dairy replacement Holstein heifers. These heifers had a very slow growth rate, were freshening at 3 years of age, had constant nasal discharge, and neck and shoulders were bare. Several liver assays suggested copper, manganese and zinc deficiencies. Fifteen heifer calves, under two years of age, were bled and assays were run for IgG1, IgG2 and IgM antibodies. Nutrient profiles of food rations were also determined according to heifer age groupings. Heifers up to 8 months in age were receiving a different ration than those 8 months and older. Trace mineral levels were raised utilizing amino acid chelated Fe, Zn, Mn, Cu and Se as the source of mineral increase. The amino acid chelates had a ligand to metal ratio of about 2:1 and an average molecular weight which did not exceed 1000. The nutrient profiles reported in parts per million (ppm) of trace mineral in the feed ration are given in Table 4:

TABLE 4

| | PPM Mineral in Food Ration | | | | |
|---|---|---|---|---|---|
| | Fe | Zn | Mn | Cu | Se |
| 3-8 Month Heifers | | | | | |
| Initial Ration | 64 | 32 | 48 | 9 | .05 |
| Chelate Containing Ration* | 163 | 115 | 96 | 27 | .14 |
| 8-24 Month Heifers | | | | | |
| Initial Ration | 82 | 31 | 44 | 10 | .07 |
| Chelate Containing Ration* | 132 | 73 | 68 | 20 | .12 |

*PPM Mineral as Amino Acid Chelates = PPM Mineral in Chelate Containing Ration minus PPM Mineral in Initial Ration The same amino acid chelate formula was used in both Rations but at different concentrations. Six months following initiation of chelated mineral therapy, the same calves were again bled. IgM levels that had been deficient, (ranging from a low of about 0.6 to a high of about 1.8 mg/ml) increased (ranging from a low of about 1.2 to a high of about 2.5) indicating an improved immune capability. Growth rates increased, nasal discharges were eliminated, pigmentation returned to hair coats and ringworm was greatly reduced to a few patches around the eyes in the heifers receiving the chelates. While, except for the IgM data, this test was largely subjective in that there was no control group, it does demonstrate the improved immune capability in these heifers attributable to the administration of the selected trace minerals iron, zinc, manganese, copper and selenium in chelated form.

EXAMPLE 3

This example also reports a field trial test relating trace mineral levels and sources to the immune response and involves Angus calves from a 110 cow herd. Over a period of several years the calves 4-12 weeks of age from this herd were experiencing a 35 to 55% morbidity and a 2-6% mortality rate from what was identified as enterotoxemia (Clostridium prefringens). Attempts to vary vaccination manufacturers, timing of vaccinations, the use of other vaccines to stimulate a better immune response and two years of copper-glycinate injections provided no relief. A nutrient profile was run on the herd feed rations. In the first test year, sixty days prior to calving, the mineral fed as free choice was changed to a ration providing iron, zinc, manganese, copper and selenium in the form of amino acid chelates. No other changes were made from the previous years. The winter during the test year was similar in temperature and snowfall to the previous years. The amino acid chelates used were the same as used in Example 2 except that the ratios of one mineral to another were modified to suit the situation. The nutrient profiles reported in parts per million (ppm) of trace mineral in the initial feed ration and in the chelated test feed ration are reported in Table 5 which follows:

TABLE 5

| | PPM Mineral in Food Ration | | | | |
|---|---|---|---|---|---|
| | Fe | Zn | Mn | Cu | Se |
| 110 Herd Angus Cows | | | | | |
| Initial Ration | 168.0 | 29.0 | 51.9 | 7.8 | .05 |
| Chelated Ration | 147.1 | 68.1 | 82.0 | 18.3 | .10 |

The changes in calf morbidity and mortality were dramatic resulting from the chelated mineral therapy. There were no calf deaths in the test year and only four calves from the herd were treated for light cases of enterotoxemia. However, surrounding herds continued to experience the same rates of morbidity and mortality as had the test herd prior to the initiation of the chelated mineral therapy. The test was extended to the following year with the same results, i.e. no calf mortality and only four calves treated for enterotoxemia.

Examples 4 and 5 which follow demonstrate the strengthening of the immune system in birds suffering from a reovirus infection causing intestinal malabsorption of nutrients. This is commonly referred to as "malabsorption syndrome" but has also been referred to by different names through the world, i.e. pale bird syndrome, femoral head necrosis, brittle bone disease, osteoporosis and infectious stunting syndrome. Malabsorption syndrome generally affects meat-producing broilers. Once an operation is infected it seems to relapse into the same syndrome batch after batch of birds. Maximum susceptibility is noted within the first seven days after hatch. In the second week, and continuing through the next five weeks, this susceptibility rapidly declines. The infections seems to be transmitted by way of the digestive system. Improper hygienic conditions and/or the stress of overcrowding seem to worsen the problem. After 4 to 6 days of incubation, approximately 20 to 30% of chicks belonging to an infected group begin to present vague signs of the syndrome. Most follow a systematic program of illness. During the second week of life, their growth rates decelerate and their limbs weaken. Their small intestines may become inflamed, thereby interfering with cation absorption, although the intensity of the enteritis varies from chick to chick. By the third week, the skeletal defects, such as enlargement of the tarsi and scars calcification of the longs bones, develop. The infected birds begin to limp and exhibit signs of rickets and osteoporosis. Frequently there is depigmentation of the skin, ruffling of feathers and diarrhea present. At the fourth week of life skeletal abberations are evident, i.e. femoral incurvation, tibial rotation deviation, thin corticals resulting in convex curving of thigh bones. *E. coli* infections and diarrhea tend to increase. By the fifth week of life the clinical symptoms seem to regress except for the skeletal alternations which may become accentuated.

Because of the malabsorption of the nutrients, the weight of the infected birds is considerably lower than birds of the same age in healthy flocks. The feed conversion index of the infected flocks rises significantly promoted by the lack of minerals in the enzyme systems. The mortality rate from the malabsorption syndrome is usually contained to about 3 to 4%, but in more severe cases it can rise to as high as 30%.

Pathological examination of the infected birds reveals underdevelopment of the thymus glands, excessive heart fluid, inflammation of the heart muscle, lesions of the liver, inflammation of the intestinal pouches with accompanying discharges (catarrhal entero typhlitis) of variable intensity. Undigested food may be present along with a yellow-orange mucus in the small distal region. There is often inflammation and/or atrophy of the pancreas, lymphatic organs and gizzard musculature. Temporary blockage of the pancreatic ducts leading to the duodenum and changes in the intestinal epithelium may occur. Hematochemical and physiopathological examinations reveal a reduction of carotenoid plasma and of fat soluble vitamins. Hematic Ca, P, Na, K and Cl may be within normal levels but, in most cases, Ca, P, glucose, total protein, albumin, urea and uric acid levels were significantly decreased over levels found in healthy birds.

Many causes for malabsorption syndrome have been suggested including mycosis (fungus) and *E. coli* (as a promoter of diarrhea) as the causes. *Pasteurella anatipestifer* and Staphylococcus infections have been noted. However, the most recent etiological studies conducted on the malabsorption syndrome and analogous forms have revealed the presence of reoviruses, adenoviruses and toga-like virus particles in the gastroenteric tracts of infected chicks. Reovirus stock have been isolated from the pancreas, the intestines, liver, the spinal cord, and femoral bone marrow of birds suffering from this disease. Almost all of the reovirus serologically correlated to the tenosynovitis virus (TVS), such as S 1133. It has been possible to reproduce gastroenteric, pancreatic and hepatic lesions by using many of the isolated reovirus even though the results are not always consistent. However, the presence of these lesions explain the digestive compromise and absorption defects of the birds. Secondary deficiency phenomena including the inability to absorb nutrients, such as minerals and fat soluble vitamins, result from the infection.

Although, the viral agents are believed to be primarily responsible for the malabsorption syndrome, there may also be other contributing factors including other viral or bacterial infections, improper nutrition and even flock management causing excessive stress. The additional viral and bacterial insults may develop after a breakdown in the immune system resulting from the malabsorption.

The following examples illustrate the benefits of the administration of selected minerals to chicks infected with the reovirus thought to be responsible for malabsorption syndrome.

EXAMPLE 4

Five hundred day-old chicks were infected with the reovirus and were arbitrarily divided on an odd/even basis into two groups of 250 birds each. Except for different mineral formulations in their feed, both groups had identical feed and housing conditions. The treated group had a 0.10% concentration of an amino acid chelate mixture containing 9% iron, 3% zinc, 1.2% manganese, 2.2% copper and 0.08% cobalt mixed in their feed. As in previous examples, the amino acid chelates had a ligand to metal ratio of about 2:1 and an average molecular weight which did not exceed 1000. The control group received the same amount of iron, zinc, manganese, copper and cobalt as inorganic salts.

Within 4 to 6 days after exposure, the control group began showing the usual signs associated with malabsorption syndrome. Skeletal alterations occurred and some enteritis was also present. Growth rates were reduced. Mortality in the control group was 3.2%.

In the treated group, after exhibiting initial malabsorption syndrome symptoms, the chicks returned to normal health and grew at equivalent or better rates than expected for normal healthy non-infected chicks, even though clinical data indicated that the reovirus remained present. Growth rate comparisons were based on the usual growth rates normally attained in this operation.

These results indicate that chicks infected with reovirus can develop equally as well as non-infected normal chicks when the infected chicks are receiving the required minerals, iron, zinc, manganese and copper in the form of amino acid chelates. The mortality and morbidity of chelate-treated chicks and uninfected chicks was no different because the amino acid chelates were helpful in maintaining the proper functioning of the immune system of the birds. It is believed the bolstering of the immune system of the treated infected chicks is primarily due to the fact that the chelates are absorbed at a site in the intestine different from the cation absorption site and the chelate site is not as negatively impacted by the reovirus as is the usual cation absorption site.

The ability of amino acid chelated minerals to protect chicks from malabsorption syndrome by means of administration of the proper minerals to laying hens is demonstrated in the following example. The rational for the experiment reported in this example was based on the fact that, to overcome the effects of malabsorption, the chick must either rely on minerals supplied to it before hatch, or consume them in a highly available chelated form shortly following hatch, as demonstrated in the preceding example. Research has shown a higher deposition of minerals into the egg when the laying hen is fed amino acid chelated minerals. The following example illustrates that this higher mineral egg content, resulting from administration of chelated minerals, additionally helps prevent malabsorption syndrome.

EXAMPLE 5

In this example, 1,000 hens of similar age from five commercial breeder coops were used. Each coop had a past history of repeated malabsorption syndrome within their respective flocks. The breeder hens in each coop were divided into two groups and maintained in wire cages. The treated group received the same formulation of amino acid chelates used in Example 4, above, at the same 0.10% concentration throughout the entire period of the experiment. The control group received the same amount of minerals in inorganic salt form.

During the 20 week trial period, both groups of hens hatched about the same total number of eggs, 46,950 for the treated group and 46,500 for the control group. The eggs were hatched under heat lamps. The percent hatchability was comparable for both groups. Other than the differences in mineral formulations consumed by the laying hens, the control and treated groups were the same. The hatched chicks from both groups were treated the same.

When the baby chicks were hatched they were closely observed for the first three weeks which is the most critical period for the malabsorption syndrome. The mortality data from this experiment is shown in Tables 6 and 7. Table 6 reports data from the control study and Table 7 reports corresponding data from the treated study utilizing amino acid chelates.

TABLE 6

| Mortality Rates of Chicks from Control Hens | | | | |
|---|---|---|---|---|
| Number of Chicks | Mortality 1st Week | Mortality 2nd Week | Mortality 3rd Week | Mortality Percent |
| 10,000 | 328 | 834 | 36 | 11.98 |
| 9,500 | 331 | 201 | 40 | 6.02 |
| 9,000 | 409 | 80 | 36 | 5.83 |
| 9,000 | 354 | 73 | 38 | 5.16 |
| 9,450 | 172 | 138 | 35 | 3.65 |
| 46,950 | 1,594 | 826 | 185 | 5.54 |

TABLE 7

| Mortality Rates of Chicks from Treated Hens | | | | |
|---|---|---|---|---|
| Number of Chicks | Mortality 1st Week | Mortality 2nd Week | Mortality 3rd Week | Mortality Percent |
| 9,000 | 130 | 61 | 35 | 2.17 |
| 9,500 | 128 | 58 | 37 | 2.35 |

TABLE 7-continued

| Mortality Rates of Chicks from Treated Hens | | | | |
|---|---|---|---|---|
| Number of Chicks | Mortality 1st Week | Mortality 2nd Week | Mortality 3rd Week | Mortality Percent |
| 9,500 | 152 | 57 | 34 | 2.55 |
| 9,500 | 150 | 59 | 38 | 2.60 |
| 9,000 | 101 | 42 | 36 | 1.98 |
| 46,500 | 661 | 277 | 180 | 2.40 |

From the above data it can be seen that, during the first week of life, the mortality of the control group was 2.41 times that of the treated group. In the second week of life, the mortality of the control group was 2.98 times that of the treated group. More than twice as many chicks which hatched from laying hens which did not receive the amino acid chelated minerals died as did chicks hatched from the treated group. Postmortem examinations of a sampling of the dead chicks in both groups indicated that they were infected with the reovirus and were suffering from malabsorption syndrome. The rates of growth among the survivors in both groups were not statistically different.

The data in the above two examples corroborate that there was a nutritional deficiency of specific trace minerals associated with the malabsorption syndrome and that this problem could be circumvented by the administration of selected minerals as amino acid chelates at the appropriate times.

The above examples demonstrate, in cases of antigenic morbidity where trace mineral malabsorption is present, that even though the antigen remains present, the necessary minerals administered in the form of amino acid chelates were absorbed whereas, inorganic mineral salts were not. This absorption allowed the immune system of the animal to be strengthened and the animal to return to a relatively normal degree of health through activation of a more viable immune system even though no drugs were given to destroy or weaken the effect of the pathogen.

It is therefore thought that, in cases of antigenic morbidity where there is trace mineral metabolic dysfunction, there are far reaching advantages to be obtained by circumventing the cationic absorption site for the absorption of minerals by chelating such minerals with amino acids and promoting their subsequent uptake in the jejunum via the dipeptide absorption sites. One particular advantage of this route of mineral supplementation may be in the case of HIV infected patients where the infection may become dominant at such time as the malabsorption syndrome develops and limit the uptake of essential minerals via the duodenum. The lack of minerals such as copper, zinc and manganese results in a compromise of the immune system. As demonstrated in the examples above, administration of these minerals, in amino acid chelated form, increased production of IgG and IgM antibodies, enhanced the functions of the immune system and lowered morbidity and mortality in bovine species.

It is therefore believed that the ingestion of effective amounts of essential minerals administered as amino acid chelates to warm-blooded animal species may enhance the immune system in animals suffering from antigenic morbidity where there is an additional metabolic compromising of trace mineral absorption. This enhancement may occur by (1) bypassing the duodenal area of the small intestine which is highly affected by trace mineral malabsorption when the minerals are in cationic form, (2) deferring absorption to the jejunum, where the amino acid chelates are absorbed as dipeptide-like molecules; and (3) ultimately increasing the uptake of the minerals through this more bioavailable form to assist the natural immune system in remaining operable and thus able to control the pathological effects in the body brought on by compromised metabolic functions in the body. It is thought that, in the case of HIV infections, that the immune system can be strengthened, thereby arresting opportunistic infections and allowing the patient to remain in the WR3 stage for an indefinite period of time. Work is continuing in this area to provide documentation.

While the above provides a detailed description of the invention and the best mode of practicing it to the extent that it has been developed, the invention is not to be limited solely to the description and examples. There are modifications which may become apparent to one skilled in the art in view of the description contained herein. Therefore, the invention is to be limited in scope only by the following claims and their functional equivalents.

We claim:

1. A method for maintaining the immune system of a warm-blooded animal afflicted with a form of antigenic morbidity which comprises the steps:
    (1) confirming the presence of an antigenic morbidity in said animal,
    (2) determining which trace minerals selected from the group consisting of copper, zinc, manganese, iron and selenium are needed to maintain the immune system of said animal,
    (3) providing a composition containing effective amounts of said trace minerals from step (2) in the form of amino acid chelates having a ligand to mineral ratio of at least 1:1, a molecular weight of no more than 1500 and a stability constant of between about $10^6$ and $10^{16}$ and
    (4) administering said composition to said warm-blooded animal.

2. A method according to claim 1 wherein said ligand to mineral ratio is 2:1 or greater.

3. A method according to claim 2 wherein said chelate has a molecular weight no greater than about 1000.

4. A method according to claim 3 wherein said composition is administered orally.

5. A method according to claim 4 wherein said composition is administered in the food of said animal.

6. A method according to claim 5 wherein said composition is continuously available to said animal.

7. A method according to claim 4 wherein said composition is administered in unit dosage form.

8. A method according to claim 4 wherein said antigenic morbidity is caused by a virus.

9. A method according to claim 8 wherein the virus has resulted in intestinal malabsorption of one or more of the required minerals when administered in ionic form.

10. A method according to claim 4 wherein the trace minerals to administer and the effective amount of trace minerals in said composition are determined by reference to collected data of mineral amounts and ratios found in animals afflicted by said antigenic morbidity and compared to mineral amounts and ratios found in healthy animals of the same species.

11. A method for alleviating symptoms of antigenic morbidity in warm-blooded animals exacerbated by intestinal malabsorption of minerals by providing said minerals in a form wherein they are absorbed from a portion of the intestinal tract other than that utilized for the absorption of cations which comprises the steps,
    (1) confirming the presence of intestinal malabsorption in an animal having symptoms of antigenic morbidity,
    (2) determining which trace minerals selected from the group consisting of copper, zinc, manganese, iron and selenium are needed to alleviate symptoms of antigenic morbidity in said animal,
    (3) providing a composition containing effective amounts of said trace minerals from step (2) in the form of amino acid chelates having a ligand to mineral ratio of at least 1:1, a molecular weight of no more than 1500 and a stability constant of between about $10^6$ and $10^{16}$ and
    (4) administering said composition to said warm-blooded animal.

12. A method according to claim 11 wherein said ligand to mineral ratio is 2:1 or greater.

13. A method according to claim 12 wherein said chelate has a molecular weight no greater than about 1000.

14. A method according to claim 13 wherein said composition is administered orally.

15. A method according to claim 14 wherein said composition is administered in the food of said animal.

16. A method according to claim 15 wherein said composition is continuously available to said animal.

17. A method according to claim 14 wherein said composition is administered in unit dosage form.

18. A method according to claim 14 wherein said symptoms of antigenic morbidity exacerbated by intestinal malabsorption of minerals are caused by a virus.

19. A method according to claim 14 wherein the trace minerals to administer and the effective amount of trace minerals in said composition are determined by reference to collected data of mineral amounts and ratios found in animals afflicted by said symptoms of antigenic morbidity and compared to mineral amounts and ratios found in healthy animals of the same species not suffering from intestinal malabsorption of minerals.

* * * * *

UNITED STATES PATENT AND TRADEMARK OFFICE
CERTIFICATE OF CORRECTION

PATENT NO.   :   5,162,369
DATED        :   November 10, 1992
INVENTOR(S)  :   H. DeWayne Ashmead, et al It is certified that error appears in the above-indentified patent and that said Letters Patent is hereby corrected as shown below:

On the title page, Item [75] "H. Dewayne Ashmead" should read --H. DeWayne Ashmead--.

Signed and Sealed this

Eighteenth Day of January, 1994

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO. : 5,162,369
DATED : November 10, 1992
INVENTOR(S) : H. DeWayne Ashmead, et al.

It is certified that error appears in the above-indentified patent and that said Letters Patent is hereby corrected as shown below:

On the title page, item [73], the Assignee is "Brigham Young University, Provo, Utah", and should read --Albion International, Inc., Clearfield, Utah".

Signed and Sealed this

Twenty-ninth Day of March, 1994

Attest:

BRUCE LEHMAN

*Attesting Officer*     *Commissioner of Patents and Trademarks*